United States Patent [19]

Hirdler et al.

[11] 4,223,140

[45] Sep. 16, 1980

[54] SOLVENT RECOVERY FROM GASEOUS MIXTURES PRODUCED IN THE MANUFACTURE OF CYANURIC ACID

[75] Inventors: Louis C. Hirdler; Raymond J. Smialek, both of Lake Charles, La.

[73] Assignee: Olin Corporation, New Haven, Conn.

[21] Appl. No.: 68,127

[22] Filed: Aug. 20, 1979

[51] Int. Cl.$^2$ .......................................... C07D 251/32
[52] U.S. Cl. ................................................. 544/192
[58] Field of Search ........................................ 544/192

[56] References Cited

U.S. PATENT DOCUMENTS 4,167,631  9/1979  Schouteten ........................... 544/192

*Primary Examiner*—John M. Ford

*Attorney, Agent, or Firm*—James B. Haglind; Donald F. Clements

[57] ABSTRACT

A process is provided for solvent recovery from a hot gaseous mixture comprised of ammonia, carbon dioxide, cyanuric acid particles, and solvent vapors. The process comprises scrubbing the hot gaseous mixture with a liquid solvent to remove the cyanuric acid particles and to form a scrubbed gaseous mixture. The scrubbed gaseous mixture is cooled to form condensed liquid solvent and a cooled gaseous mixture containing traces of the solvent. The temperature of the cooled gaseous mixture is kept above that at which ammonium carbamate is formed by the reaction of ammonia with carbon dioxide. Condensed liquid solvent is separated from the cooled gaseous mixture and the cooled gaseous mixture is contacted with additional liquid solvent to form a substantially solvent-free gaseous mixture.

8 Claims, 1 Drawing Figure

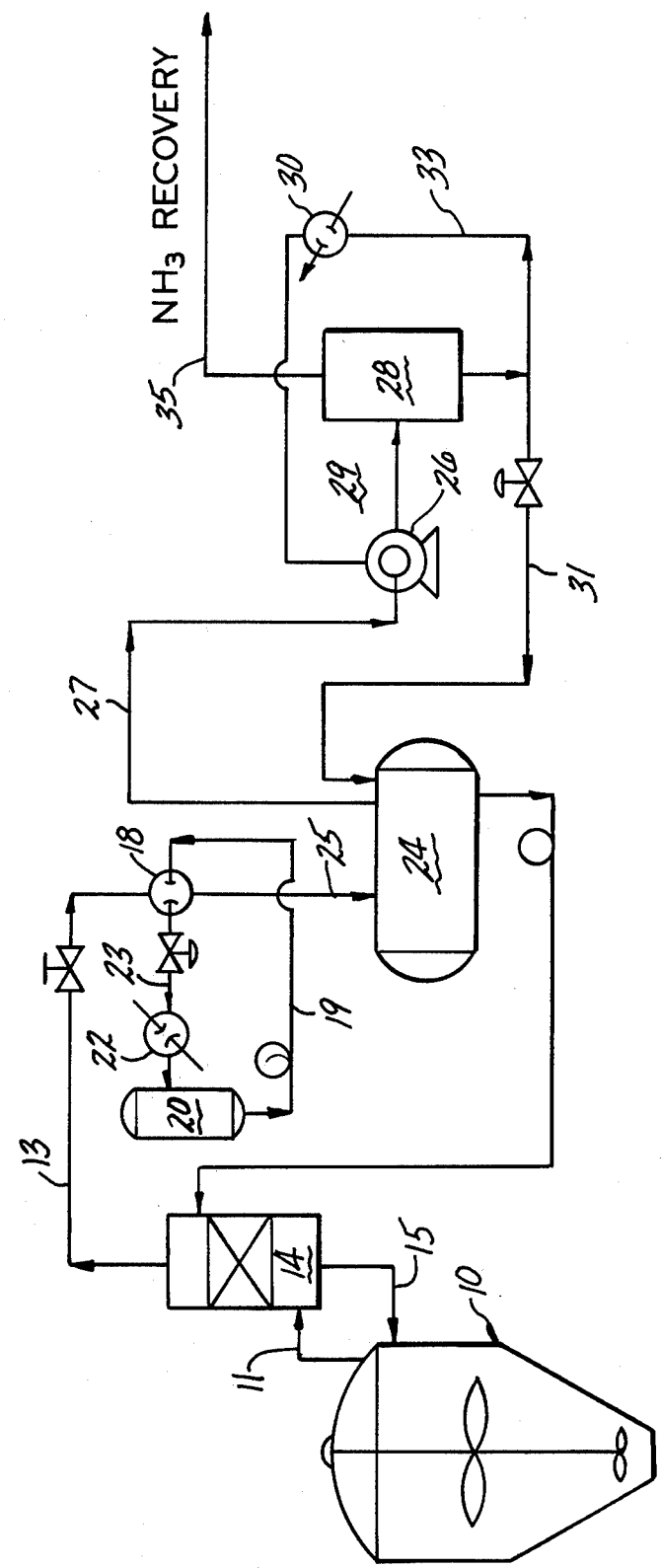

SOLVENT RECOVERY FROM GASEOUS MIXTURES PRODUCED IN THE MANUFACTURE OF CYANURIC ACID

This invention relates to the production of cyanuric acid. More particularly, this invention relates to the production of cyanuric acid from the pyrolysis of urea in a solvent.

Cyanuric acid can be produced by heating urea or biuret in a solvent medium. During the process, solid particles of cyanuric acid are formed in the hot solvent. Copious amounts of ammonia gas are also produced along with small amounts of carbon dioxide gas. The evolving ammonia and carbon dioxide in combination with hot solvent vapors form a gaseous mixture which also contains entrained cyanuric acid particles. To operate the process economically, it is necessary to efficiently recover the solvent from this gaseous mixture.

Ammonia and carbon dioxide in the gaseous mixture may, under suitable conditions, react to form ammonium carbamate which is deposited as a solid at temperatures of about 60° C. at atmospheric pressure. Condensation procedures must be used which prevent the plugging and blockage of lines and equipment with deposits of ammonium carbamate.

It is an object of the process of the present invention to efficiently recover solvents from gaseous mixtures produced during the manufacture of cyanuric acid.

Another object of the present invention is to provide a process which prevents the deposition of ammonium carbamate on equipment and pipe line surfaces.

These and other objects of the invention are accomplished in a process for solvent recovery from a hot gaseous mixture comprised of ammonia, carbon dioxide, cyanuric acid particles, and solvent vapors, the solvent having a boiling point in the range of from about 150° to about 300° C., the process which comprises:

(a) scrubbing the hot gaseous mixture with liquid solvent to remove the cyanuric acid particles and to form a scrubbed gaseous mixture, (b) cooling the scrubbed gaseous mixture with a coolant to form condensed liquid solvent and a cooled gaseous mixture containing traces of solvent, the temperature of the cooled gaseous mixture being above that at which ammonium carbamate is formed by the reaction of said ammonia with said carbon dioxide, (c) separating the condensed liquid solvent from the cooled gaseous mixture, and (d) contacting the cooled gaseous mixture with additional liquid solvent to remove the traces of solvent from the cooled gaseous mixture to form a substantially solvent-free gaseous mixture.

The FIGURE represents a flow diagram of the process of the present invention.

Cyanuric acid is produced in reactor 10 by the pyrolysis of urea in a hot solvent. During the pyrolysis process, cyanuric acid particles are produced. Also produced is a hot gaseous mixture of ammonia, carbon dioxide, and solvent vapors with entrained cyanuric acid particles. The hot gaseous mixture is passed from reactor 10 to scrubber 14 through line 11. In scrubber 14, cyanuric acid particles along with a portion of the solvent vapors are removed from the gaseous mixture by contacting the mixture with solvent from tank 24. A scrubbed gaseous mixture exits scrubber 14 and passes through line 13 to condenser 18. The scrubbing solvent is returned to reactor 10 through line 15.

Cooling the gas mixture in condenser 18 is a coolant supplied by tank 20 through line 19. The coolant is returned through line 23 to cooler 22 and to tank 20. Condenser 18 cools the gas mixture and converts the solvent vapors to liquid solvent. Condensed solvent and a cooled gas mixture pass through line 25 to tank 24. The gas mixture containing traces of solvent is pumped from tank 24 to separator 28 by pump 26 via line 27 and line 29. Part of the solvent recovered in separator 28 is returned to tank 24 through line 31. Another part of the solvent is cooled in cooler 30 and fed to pump 26 through line 33 to be used as seal liquid for pump 26. A substantially solvent-free gas mixture is conveyed through line 35 to apparatus (not shown) for recovery of the ammonia.

In the pyrolysis process, urea is fed to a reactor containing a body of solvent. The solvent is maintained at temperatures sufficient to pyrolyze the urea, for example, in the range of from about 150° to about 300° C. During the pyrolysis process, the urea is converted to cyanuric acid in a reaction which is believed to be expressed by the following equation:

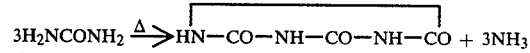

$$3H_2NCONH_2 \xrightarrow{\Delta} \overline{HN-CO-NH-CO-NH-CO} + 3NH_3$$

The solvent selected is one having a boiling point in the range of from about 150° to about 300° C. Suitable solvents include, for example, methoxy ethoxy isopropanols, tetrahydrofurfuryl alcohol, alkyl sulfones, dialkyl sulfones, dialkyl ethers of polyalkylene glycols, alkyl pyrrolidones, cycloalkyl pyrrolidones, diphenyl oxide, and alkyl oxazolidinones. A preferred solvent is N-cyclohexyl pyrrolidone.

The pyrolysis process may be operated at subatmospheric pressures, for example, from about 300 to about 759 mm, at atmospheric pressure or at superatmospheric pressure, with subatmospheric or atmospheric pressures being preferred.

Ammonia gas is also produced in large amounts along with minor amounts of carbon dioxide gas. During the reaction period, these gases mix with hot solvent vapors to form a gaseous mixture. As this hot gaseous mixture rises and separates from the reaction mixture, it entrains particles of cyanuric acid.

The hot gaseous mixture is removed from the synthesis reactor and conveyed to a scrubber. Solvent is passed countercurrently to the gaseous mixture. In a reflux process, the solvent is heated while extracting cyanuric acid particles and a portion of the solvent from the gaseous mixture. The heated solvent containing cyanuric acid particles is returned to the reactor as solvent make-up.

To recover substantial amounts of solvent from the hot gaseous mixture obtained from the scrubber, the gaseous mixture is cooled to condense the solvent as a liquid.

The solvent condensation step is carefully controlled to prevent formation of ammonium carbamate. Ammonium carbamate is believed to be produced by the reaction of ammonia with carbon dioxide according to the equation:

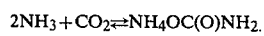

$$2NH_3 + CO_2 \rightleftharpoons NH_4OC(O)NH_2$$

For example, at temperatures below about 60° C. at atmospheric pressure, ammonium carbamate forms as a solid; at temperatures above about 60° C. at atmospheric pressure, ammonium carbamate decomposes into ammonia gas and carbon dioxide gas. To prevent deposits of solid ammonium carbamate from forming on the surfaces of process equipment such as heat exchangers, pipe lines, etc., it is necessary to keep the temperature of the gaseous mixture above that at which ammonium carbamate is formed. This is accomplished, for example, by controlling the temperature of equipment surfaces directly in contact with the cooled gaseous mixture.

In one embodiment, the hot gaseous mixture is condensed using a tempered cooling system which is employed, particularly where widely varying heat loads are to be handled by the condenser. A cooling fluid at a constant temperature, which will condense the solvent vapors, but prevent the formation of deposits of ammonium carbamate, is supplied to the condenser. As shown in the FIGURE, the temperature of the coolant is adjusted in an external cooling loop by cooler 22 and the coolant is pumped through tank 20 to gaseous mixture condenser 18. Suitable coolants for use in the tempered cooling system include glycols, aqueous glycol solutions, water and commercial heat transfer fluids such as DOWTHERM ® heat transfer agents (Dow Chemical Co.) or THERMINOL ® heat transfer fluids (Monsanto Co.).

Following the condensation step, the cooled gaseous mixture is at a temperature corresponding to those in the range of from about 60° to about 75° C., and preferably from about 60° to about 65° C. at atmospheric pressure. The cooled gaseous mixture contains less than about 5 and preferably less than about 3 percent by weight of solvent.

From the condenser, the gaseous mixture and condensed solvent are passed to a separating tank. The condensed solvent is pumped to the scrubber to be used in the refluxing of the hot gaseous mixture. The gaseous mixture containing traces of solvent is contacted with additional solvent to recover additional amounts of solvent. This may be accomplished by pumping the cooled gaseous mixture from the separating tank to a second scrubber where contact with solvent removes solvent from the gaseous mixture. In a preferred embodiment, the cooled gaseous mixture is drawn to the suction end of a liquid-ring vacuum pump in which the solvent is used as seal liquid. The seal liquid absorbs substantially all of the residual solvent present in gaseous mixture. This simplifies the solvent recovery process by not requiring the separation of the solvent from a different liquid. During the separation, the gaseous mixture is maintained at a temperature corresponding to that above about 60° C. at atmospheric pressure. The gaseous mixture and seal liquid are pumped to a separator where the solvent-free gases are removed and passed through a heated line to the ammonia recovery area. Seal liquid is also recovered and cooled in a cooler before being returned to the vacuum pump.

The novel process of the present invention recovers essentially all of the solvent from the gaseous mixture. The gaseous mixture of ammonia and carbon dioxide recovered contains less than about 1 percent and preferably less than 0.2 percent by weight of solvent vapors.

Further, the novel process of the present invention permits the recovery of solvent values without incurring the undesired formation of deposits of ammonium carbamate on the surfaces of heat exchangers, pipe lines, and other gas processing equipment.

In addition, the process of the present invention recovers substantial energy values through the heating of the solvent by the hot gaseous mixture during the scrubbing step.

The novel process of the present invention is further illustrated by the following example.

EXAMPLE

Molten urea is fed to a reaction vessel containing hot N-cyclohexyl pyrrolidone as the solvent. The urea is pyrolyzed at subatmospheric pressures to produce a hot slurry containing cyanuric acid crystals. Also produced during the pyrolysis reaction is ammonia gas and minor amounts of carbon dioxide. These gases contact hot solvent vapors to form a hot gaseous mixture which, as it forms above the reaction mixture, entrains particles of cyanuric acid. The hot gaseous mixture is removed from the reaction vessel and conveyed to a scrubber. N-cyclohexyl pyrrolidone at an initial temperature of 65° C. is passed countercurrently to the hot gaseous mixture to produce a reflux which removes cyanuric acid particles. Heated solvent from the scrubber is returned to the reaction vessel for producing cyanuric acid. The hot gaseous mixture is passed to a condenser cooled with a tempered coolant. Dowtherm J ® heat transfer fluid at a temperature of 50° C. is fed to the condenser to cool the gaseous mixture to a temperature of 65° C. and condense the solvent vapors. Hot Dowtherm J ® is removed from the condenser and fed to a water cooled cooler to cool the Dowtherm J ® to 50° C. and then fed to a heat transfer fluid surge tank. Condensed solvent and the gaseous mixture pass to an accumulator tank. The condensed solvent is pumped back to the scrubber for use as the scrubbing liquid. From the accumulator tank, the cooled ammonia-carbon dioxide gas mixture is drawn into a vacuum pump. The vacuum pump is a liquid-ring type which uses N-cyclohexyl pyrrolidone as the seal liquid. Residual solvent in the gaseous mixture is absorbed by the seal liquid and both fluids are pumped into a separator tank. Ammonia-carbon dioxide gas mixture at atmospheric pressure is passed through heated lines to the ammonia recovery unit. The gas contains less than 0.2 percent by weight of solvent.

Seal liquid is passed from the separator tank through a cooler using cold water as the coolant to reduce its temperature to 60° C. The cooled seal liquid is then returned to the vacuum pump.

What is claimed is:

1. A process for solvent recovery from a hot gaseous mixture comprised of ammonia, carbon dioxide, cyanuric acid particles, and solvent vapors, said solvent having a boiling point in the range of from about 150° to about 300° C., said process which comprises:
    (a) scrubbing said hot gaseous mixture with liquid solvent to remove said cyanuric acid particles and to form a scrubbed gaseous mixture,
    (b) cooling said scrubbed gaseous mixture with a coolant to form condensed liquid solvent and a cooled gaseous mixture containing traces of solvent, the temperature of said cooled gaseous mixture being above that at which ammonium carbamate is formed by the reaction of said ammonia with said carbon dioxide,
    (c) separating said condensed liquid solvent from said cooled gaseous mixture, and (d) contacting said cooled gaseous mixture with additional liquid solvent to remove said traces of solvent from said cooled gaseous mixture to form a substantially solvent-free gaseous mixture.

2. The process of claim 1 in which said solvent is selected from the group consisting of methoxy ethoxy isopropanols, tetrahydrofurfuryl alcohol, alkyl sulfones, dialkyl sulfones, dialkyl ethers of polyalkylene glycols, alkyl pyrrolidones, cycloalkyl pyrrolidones, diphenyl oxide, and alkyl oxazolidinones.

3. The process of claim 1 in which said coolant is selected from the group consisting of glycols, aqueous glycol solutions, water, and commercial heat transfer fluids.

4. The process of claim 3 in which said cooled gaseous mixture contains less than about 5 percent by weight of said solvent.

5. The process of claim 2 in which said solvent is cyclohexyl pyrrolidone.

6. The process of claim 5 in which said additional liquid solvent in step (d) comprises the seal liquid employed in a vacuum pump.

7. The process of claim 6 in which said substantially solvent-free gaseous mixture contains less than about 0.2 percent by weight of said solvent.

8. The process of claim 2, 3 or 6 in which said cooled gaseous mixture is at a temperature in the range of from about 60° to about 75° C.

* * * * *